United States Patent
Shalyaev et al.

(10) Patent No.: US 6,372,683 B2
(45) Date of Patent: Apr. 16, 2002

(54) METHOD AND CATALYST SYSTEM FOR PRODUCING AROMATIC CARBONATES

(75) Inventors: Kirill Vladimirovich Shalyaev, Clifton Park; Grigorii Lev Soloveichik, Latham; Bruce Fletcher Johnson, Scotia; Donald Wayne Whisenhunt, Jr., Niskayuna, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/757,247

(22) Filed: Jan. 10, 2001

Related U.S. Application Data

(62) Division of application No. 09/495,539, filed on Jan. 31, 2000, now Pat. No. 6,207,849.

(51) Int. Cl.[7] .................. B01J 31/00; B01J 27/128; B01J 23/00; B01J 23/02; C07C 69/96

(52) U.S. Cl. .................. 502/150; 502/152; 502/229; 502/230; 502/302; 502/304; 502/323; 502/331; 502/324; 502/343; 502/345; 502/350; 558/270; 558/271; 558/272; 558/273; 558/274

(58) Field of Search .................. 502/302, 304, 502/324, 323, 331, 343, 345, 350, 229, 230, 150, 152; 558/270–274

(56) References Cited

U.S. PATENT DOCUMENTS

| | | |
|---|---|---|
| 4,187,242 A | 2/1980 | Chalk |
| 5,231,210 A | 7/1993 | Joyce et al. ................ 558/274 |
| 5,239,106 A | 8/1993 | Shafer ........................ 558/274 |
| 5,284,964 A | 2/1994 | Pressman et al. ........... 558/260 |
| 5,373,083 A | 12/1994 | King et al. .................. 528/199 |
| 5,380,907 A | 1/1995 | Mizukami et al. .......... 558/270 |
| 5,399,734 A | 3/1995 | King et al. .................. 558/270 |
| 5,498,789 A | 3/1996 | Takagi et al. ............... 558/270 |
| 5,502,232 A | 3/1996 | Buysch et al. .............. 558/270 |
| 5,543,547 A | 8/1996 | Iwane et al. ................ 558/274 |
| 5,726,340 A * | 3/1998 | Takagi et al. ............... 558/274 |
| 5,760,272 A * | 6/1998 | Pressman et al. ........... 558/274 |
| 5,821,377 A | 10/1998 | Buysch et al. .............. 558/274 |
| 5,856,554 A * | 1/1999 | Buysch et al. .............. 558/274 |
| 6,160,154 A * | 12/2000 | Spivack et al. ............. 558/274 |
| 6,175,032 B1 * | 1/2001 | Patel et al. .................. 558/274 |
| 6,184,409 B1 * | 2/2001 | Patel et al. .................. 558/274 |
| 6,187,942 B1 * | 2/2001 | Patel et al. .................. 558/274 |
| 6,197,991 B1 * | 3/2001 | Spivack et al. ............. 558/274 |
| 6,201,146 B1 * | 3/2001 | Spivack et al. ............. 558/274 |
| 6,207,849 B1 * | 3/2001 | Shalyaev et al. ........... 558/274 |
| 6,215,015 B1 * | 4/2001 | Patel et al. .................. 558/274 |

FOREIGN PATENT DOCUMENTS

| | | |
|---|---|---|
| DE | 736325 | 3/1996 |
| JP | 10158221 | 6/1980 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |

* cited by examiner

*Primary Examiner*—Mark L. Bell
*Assistant Examiner*—Patricia L. Hailey
(74) *Attorney, Agent, or Firm*—Ben P. Patel; Donald S. Ingraham

(57) ABSTRACT

A method and catalyst system for producing aromatic carbonates from aromatic hydroxy compounds. In one embodiment, the method includes the step of contacting at least one aromatic hydroxy compound with oxygen and carbon monoxide in the presence of a carbonylation catalyst system having catalytic amounts of the following components: a Group VIII B metal source; a combination of inorganic co-catalysts including a copper source and at least one of a titanium source or a zirconium source; an onium chloride composition; and a base. Alternative embodiments include inorganic co-catalyst combinations of a lead source and at least one of a titanium source or a manganese source.

16 Claims, 1 Drawing Sheet

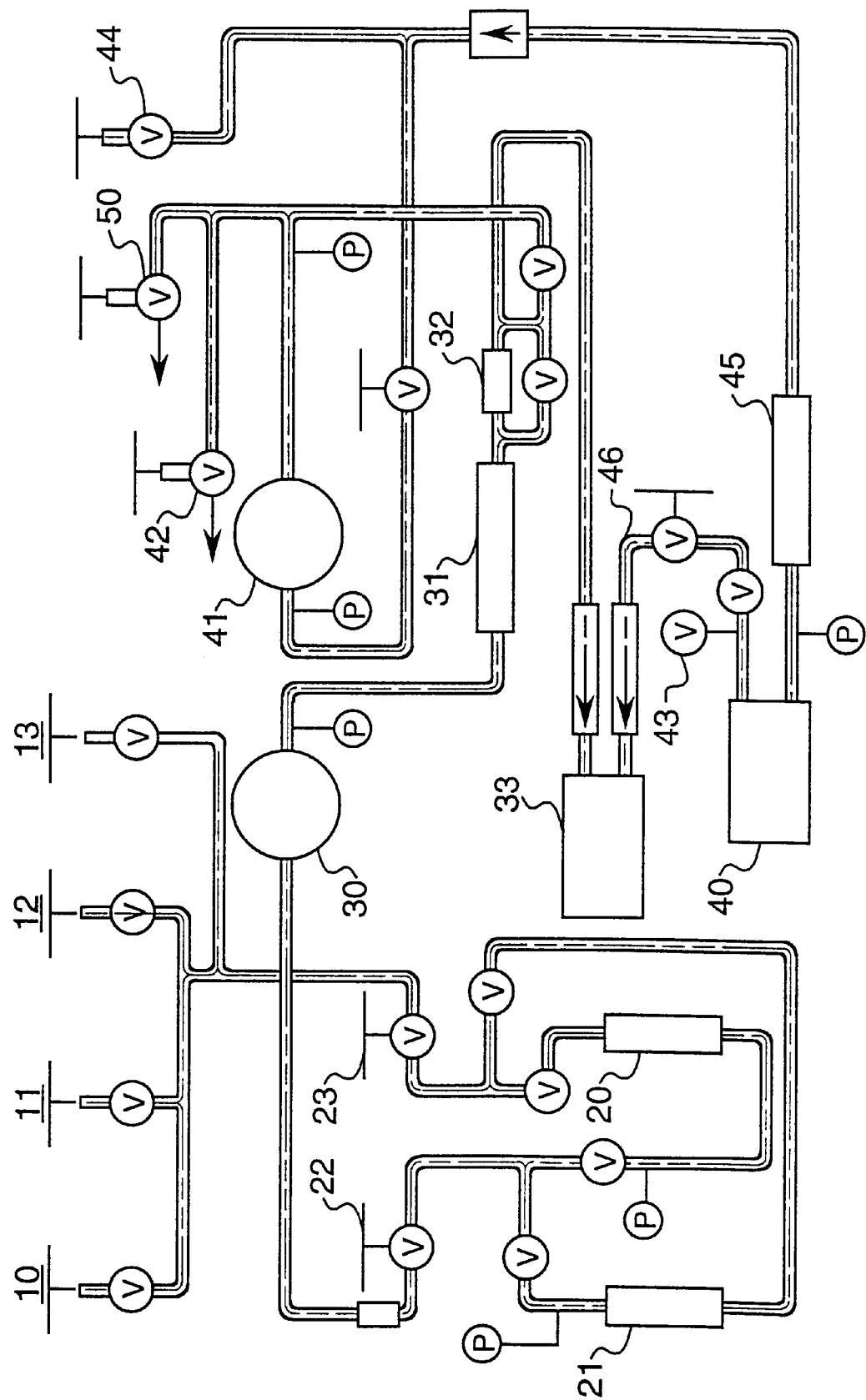

METHOD AND CATALYST SYSTEM FOR PRODUCING AROMATIC CARBONATES

This application is a division of application Ser. No. 09/495,539, filed Jan. 31, 2000, now U.S. Pat. No. 6,207,849, which is hereby incorporated by reference in its entirety.

BACKGROUND

1. Field of the Invention

The present invention is directed to a method and catalyst system for producing aromatic carbonates and, more specifically, to a method and catalyst system for producing diaryl carbonates through the carbonylation of aromatic hydroxy compounds.

2. Discussion of Related Art

Aromatic carbonates find utility, inter alia, as intermediates in the preparation of polycarbonates. For example, a popular method of polycarbonate preparation is the melt transesterification of aromatic carbonates with bisphenols. This method has been shown to be environmentally superior to previously used methods which employed phosgene, a toxic gas, as a reagent and chlorinated aliphatic hydrocarbons, such as methylene chloride, as solvents.

Various methods for preparing aromatic carbonates have been previously described in the literature and/or utilized by industry. A method that has enjoyed substantial popularity in the literature involves the direct carbonylation of aromatic hydroxy compounds with carbon monoxide and oxygen. In general, practitioners have found that the carbonylation reaction requires a rather complex catalyst system. For example, in U.S. Pat. No. 4,187,242, which is assigned to the assignee of the present invention, Chalk reports that a carbonylation catalyst system should contain a Group VIII B metal, such as ruthenium, rhodium, palladium, osmium, iridium, platinum, or a complex thereof. Further refinements to the carbonylation reaction include the identification of organic co-catalysts, such as terpyridines, phenanthrolines, quinolines and isoquinolines in U.S. Pat. No. 5,284,964 and the use of certain halide compounds, such as quaternary ammonium or phosphonium halides in U.S. Pat. No. 5,399,734, both patents also being assigned to the assignee of the present invention.

The economics of the carbonylation process is strongly dependent on the number of moles of aromatic carbonate produced per mole of Group VIII B metal utilized (i.e. "catalyst turnover"). Consequently, much work has been directed to the identification of efficacious catalyst combinations that increase catalyst turnover. In U.S. Pat. No. 5,231,210, which is also assigned to the present assignee, Joyce et al. report the use of a cobalt pentadentate complex as an inorganic co-catalyst ("IOCC"). In U.S. Pat. No. 5,498,789, Takagi et al. report the use of lead as an IOCC. In U.S. Pat. No. 5,543,547, Iwane et al. report the use of trivalent cerium as an IOCC. In U.S. Pat. No. 5,726,340, Takagi et al. report the use of lead and cobalt as a binary IOCC system.

Carbonylation catalyst literature lauds the effectiveness of bromide compounds as a halide source in the catalyst system. For example, in the aforementioned U.S. Pat. No. 5,543,547, Iwane et al. state the traditional understanding that bromide sources are the preferred halide sources and that chloride is known to exhibit low activity. While it is true that bromide has historically exhibited higher activity, there are drawbacks to using bromide in the carbonylation reaction. Initially, it is worth noting that onium bromide compounds are typically expensive compared to, e.g., onium chloride compounds. Furthermore, when used to carbonylate phenol, bromide ion is consumed in the process forming undesirable brominated byproducts, such as 2- and 4- bromophenols and bromo diphenylcarbonate. These byproducts must typically be recovered and recycled, further adding to the investment and operating cost of the process. However, due to their comparatively low activity, onium chloride compounds have not traditionally been considered an economically viable alternative to onium bromide compounds.

Unfortunately, the literature is not instructive regarding the role of many catalyst components in the carbonylation reaction (i.e. the reaction mechanism). Accordingly, meaningful guidance regarding the identification of effective combinations of catalyst system components is cursory at best. In this regard, periodic table groupings have failed to provide guidance in identifying additional IOCC's. For example, U.S. Pat. No. 5,856,554 provides a general listing of possible IOCC candidates, yet further analysis has revealed that many of the members (and combinations of members) of the recited groups (i.e., Groups IV B and V B) do not effectively catalyze the carbonylation reaction. Therefore, due to the lack of guidance in the literature, the identification of effective carbonylation catalyst systems has become a serendipitous exercise.

As the demand for high performance plastics has continued to grow, new and improved methods of providing product more economically are needed to supply the market. In this context, various processes and catalyst systems are constantly being evaluated; however, the identities of improved and/or additional effective catalyst systems for these processes continue to elude the industry. Consequently, a long felt, yet unsatisfied need exists for new and improved methods and catalyst systems for producing aromatic carbonates and the like.

SUMMARY OF THE INVENTION

Accordingly, the present invention is directed to a method and catalyst system for producing aromatic carbonates. In one embodiment, the method includes the step of contacting at least one aromatic hydroxy compound with oxygen and carbon monoxide in the presence of a carbonylation catalyst system having catalytic amounts of the following components: a Group VIII B metal source; a combination of inorganic co-catalysts including a copper source and at least one of a titanium source or a zirconium source; an onium chloride composition; and a base.

In various alternative embodiments, the carbonylation catalyst system can include catalytic amounts inorganic co-catalyst combinations of a lead source and at least one of a titanium source or a manganese source.

BRIEF DESCRIPTION OF THE DRAWING

Various features, aspects, and advantages of the present invention will become more apparent with reference to the following description, appended claims, and accompanying drawing, wherein the FIGURE is a schematic view of a device capable of performing an aspect of an embodiment of the present invention.

DETAILED DESCRIPTION OF PREFERRED EMBODIMENTS

The present invention is directed to a method and catalyst system for producing aromatic carbonates. In one embodiment, the method includes the step of contacting at least one aromatic hydroxy compound with oxygen and carbon monoxide in the presence of a carbonylation catalyst system having catalytic amounts of the following components: a Group VIII B metal source; a combination of inorganic co-catalysts; an onium chloride composition; and a base.

For convenience, the constituents of the catalyst system described herein are called "components" irrespective of whether a reaction between specific components actually occurs either before or during the carbonylation reaction. Therefore, the catalyst system may include the components and any reaction products thereof.

Unless otherwise noted, the term "catalytic amount," as used herein, includes that amount of a component capable of either increasing (directly or indirectly) the yield of the carbonylation product or increasing selectivity toward an aromatic carbonate. Optimum amounts of a given component can vary based on reaction conditions and the identity of other components, yet can be readily determined in light of the discrete circumstances of a given application.

Aromatic hydroxy compounds which may be used in the present process include aromatic mono or polyhydroxy compounds, such as phenol, cresol, xylenol, resorcinol, hydroquinone, and bisphenol A. Aromatic organic mono hydroxy compounds are preferred, with phenol being more preferred.

In various preferred embodiments, the carbonylation catalyst system contains at least one constituent from the Group VIII B metals or a compound thereof. A preferred Group VIII B constituent is a catalytic amount of a palladium source. The palladium source may be a non-supported Pd(II) salt or complex. As used herein, the term "non-supported" indicates the absence of industrially conventional catalyst supports based on carbon, element oxides, element carbides or element salts in various presentations. Examples of supports containing carbon are coke, graphite, carbon black and activated carbon. Examples of element oxide catalyst supports are $SiO_2$ (natural or synthetic silicas, quartz), $Al_2O_3$ ($\alpha$-, $\gamma$- $Al_2O_3$), aluminas, natural and synthetic aluminosilicates (zeolites), $TiO_2$ (rutile, anatase), $ZrO_2$ and $ZnO$. Examples of element carbides and salts are SiC, $AlPO_4$, $BaSO_4$, and $CaCO_3$.

Accordingly, suitable palladium sources include palladium halides, nitrates, carboxylates, oxides and palladium complexes containing carbon monoxide, amines, phosphines or olefins. As used herein, the term "complex" includes coordination or complex compounds containing a central ion or atom. The complexes may be nonionic, cationic, or anionic, depending on the charges carried by the central atom and the coordinated groups. Other common names for these complexes include complex ions (if electrically charged), Werner complexes, and coordination complexes.

In various applications, it may be preferable to utilize palladium(II) salts of organic acids, including carboxylates with $C_{2-6}$ aliphatic acids. Palladium(II) acetylacetonate and dichloro(1,4-bis(diphenylphosphino)butane) palladium (II) are also suitable palladium sources. Preferably, the amount of Group VIII B metal source employed should be sufficient to provide about 1 mole of metal per 800–10,000 moles of aromatic hydroxy compound. More preferably, the proportion of Group VIII B metal source employed should be sufficient to provide about 1 mole of metal per 2,000–5,000 moles of aromatic hydroxy compound.

The carbonylation catalyst system further contains a catalytic amount of an onium chloride composition, such as an organic onium chloride salt. The salt may be a quaternary ammonium or phosphonium chloride salt, or a hexaalkylguanidinium chloride salt. In various embodiments, $\alpha$, $\omega$-bis(pentaalkylguanidinium)alkane chloride salts may be preferred. Suitable onium chloride compositions include tetrabutylammonium chloride, tetraethylammonium chloride, and hexaethylguanidinium chloride. In preferred embodiments, the carbonylation catalyst system can contain between about 5 and about 2000 moles of chloride per mole of palladium employed, and, more preferably, between about 50 and about 1000 molar equivalents of chloride are used.

The carbonylation catalyst system also includes a catalytic amount of a base. Any desired bases or mixtures thereof, whether organic or inorganic may be used. A non-exclusive listing of suitable inorganic bases include alkali metal hydroxides and carbonates; $C_2$–$C_{12}$ carboxylates or other salts of weak acids; and various alkali metal salts of aromatic hydroxy compounds, such as alkali metal phenolates. Hydrates of alkali metal phenolates may also be used. Examples of suitable organic bases include tertiary amines and the like. Preferably, the base used is an alkali metal salt incorporating an aromatic hydroxy compound, more preferably an alkali metal salt incorporating the aromatic hydroxy compound to be carbonylated to produce the aromatic carbonate. A preferred base is sodium phenoxide. In preferred embodiments, between about 5 and about 1000 molar equivalents of base are employed (relative to palladium), and, more preferably, between about 100 and about 700 molar equivalents of base are used.

The carbonylation catalyst system includes a catalytic amount of a combination of inorganic co-catalysts (IOCC's). It has been discovered that certain IOCC combinations can effectively catalyze the carbonylation reaction in the presence of the aforementioned catalyst system components. Such IOCC combinations include lead and titanium; lead and manganese; copper and titanium; and copper and zirconium. Additional IOCC's may be used in the carbonylation catalyst system, provided the additional IOCC does not deactivate (i.e. "poison") the original IOCC combination. Examples of additional IOCC's include zinc and cerium.

An IOCC can be introduced to the carbonylation reaction in various forms, including salts and complexes, such as tetradentate, pentadentate, hexadentate, or octadentate complexes. Illustrative forms may include oxides, halides, carboxylates, diketones (including beta-diketones), nitrates, complexes containing carbon monoxide or olefins, and the like. Suitable beta-diketones include those known in the art as ligands for the IOCC metals of the present system. Examples include, but are not limited to, acetylacetone, benzoylacetone, dibenzoylmethane, diisobutyrylmethane, 2,2-dimethylheptane-3,5-dione, 2,2,6-trimethylheptane-3,5-dione, dipivaloylmethane, and tetramethylheptanedione. The quantity of ligand is preferably not such that it interferes with the carbonylation reaction itself, with the isolation or purification of the product mixture, or with the recovery and reuse of catalyst components (such as palladium). An IOCC may be used in its elemental form if sufficient reactive surface area can be provided. However, it is preferable that an IOCC is non-supported as discussed above relative to the Group VII B metals.

IOCC's are included in the carbonylation catalyst system in catalytic amounts. In this context a "catalytic amount" is an amount of IOCC (or combination of IOCC's) that increases the number of moles of aromatic carbonate produced per mole of Group VIII B metal utilized; increases the number of moles of aromatic carbonate produced per mole of chloride utilized; or increases selectivity toward aromatic carbonate production beyond that obtained in the absence of the IOCC (or combination of IOCC's). Optimum amounts of an IOCC in a given application will depend on various factors, such as the identity of reactants and reaction conditions. For example, when palladium is included in the reaction, the molar ratio of copper relative to palladium at the initiation of the reaction is preferably between about 0.1 and about 100.

The carbonylation reaction can be carried out in a batch reactor or a continuous reactor system. Due in part to the low solubility of carbon monoxide in organic hydroxy compounds, such as phenol, it is preferable that the reactor vessel be pressurized. In preferred embodiments, gas can be supplied to the reactor vessel in proportions of between about 2 and about 50 mole percent oxygen, with the balance being carbon monoxide and, in any event, outside the explosion range for safety reasons. It is contemplated that oxygen can be supplied in diatomic form or from another oxygen containing source, such as peroxides and the like. Additional gases may be present in amounts that do not deleteriously affect the carbonylation reaction. The gases may be introduced separately or as a mixture. A total pressure in the range of between about 10 and about 250 atmospheres is preferred. Drying agents, typically molecular sieves, may be present in the reaction vessel. Reaction temperatures in the range of between about 60° C. and about 150° C. are preferred. Gas sparging or mixing can be used to aid the reaction.

In order that those skilled in the art will be better able to practice the present invention reference is made to the FIGURE, which shows an example of a continuous reactor system for producing aromatic carbonates. The symbol "V" indicates a valve and the symbol "P" indicates a pressure gauge.

The system includes a carbon monoxide gas inlet 10, an oxygen inlet 11, a manifold vent 12, and an inlet 13 for a gas, such as carbon dioxide. A reaction mixture can be fed into a low pressure reservoir 20, or a high pressure reservoir 21, which can be operated at a higher pressure than the reactor for the duration of the reaction. The system further includes a reservoir outlet 22 and a reservoir inlet 23. The gas feed pressure can be adjusted to a value greater than the desired reactor pressure with a pressure regulator 30. The gas can be purified in a scrubber 31 and then fed into a mass flow controller 32 to regulate flow rates. The reactor feed gas can be heated in a heat exchanger 33 having appropriate conduit prior to being introduced to a reaction vessel 40. The reaction vessel pressure can be controlled by a back pressure regulator 41. After passing through a condenser 25, the reactor gas effluent may be either sampled for further analysis at valve 42 or vented to the atmosphere at valve 50. The reactor liquid can be sampled at valve 43. An additional valve 44 can provide further system control, but is typically closed during the gas flow reaction.

In the practice of one embodiment of the invention, the carbonylation catalyst system and aromatic hydroxy compound are charged to the reactor system. The system is sealed. Carbon monoxide and oxygen are introduced into an appropriate reservoir until a preferred pressure (as previously defined) is achieved. Circulation of condenser water is initiated, and the temperature of the heat exchanger 33 (e.g., oil bath) can be raised to a desired operating temperature. A conduit 46 between heat exchanger 33 and reaction vessel 40 can be heated to maintain the desired operating temperature. The pressure in reaction vessel 40 can be controlled by the combination of reducing pressure regulator 30 and back pressure regulator 41. Upon reaching the desired reactor temperature, aliquots can be taken to monitor the reaction.

EXAMPLES

The following examples are included to provide additional guidance to those skilled in the art in practicing the claimed invention. While some of the examples are illustrative of various embodiments of the claimed invention, others are comparative and are identified as such. The examples provided are merely representative of the work that contributes to the teaching of the present application. Accordingly, these examples are not intended to limit the invention, as defined in the appended claims, in any manner. Unless otherwise specified, all parts are by weight, and all equivalents are relative to palladium. Reaction products were verified by gas chromatography. All reactions were carried out in a glass, batch reactor at 100° C. in an approximately 6–7% $O_2$ in CO atmosphere at an operating pressure of 108.9 atm. Reaction time was 3 hours for each run. Each reaction was run in replicate (3x or 4x) with the average of the replicate runs reported herein.

As discussed supra, the economics of aromatic carbonate production is dependent on the number of moles of aromatic carbonate produced per mole of Group VIII B metal utilized. In the following examples, the aromatic carbonate produced is diphenylcarbonate (DPC) and the Group VIII B metal utilized is palladium. For convenience, the number of moles of DPC produced per mole of palladium utilized is referred to as the palladium turnover number (Pd TON). Various preferred embodiments of the present method produce Pd TON of at least 1500. Even more preferred embodiments produce Pd TON of at least 2500.

Example 1

Diphenyl carbonate was produced by adding, at ambient conditions, 0.25 mM dichloro(1,4-bis(diphenylphosphino)butane) palladium(II) ["Pd(dppb)$Cl_2$"], 600 equivalents of chloride in the form of tetrabutylammonium chloride ("TBAC"), 150 equivalents of phenoxide in the form of sodium phenoxide ("NaOPh"), and an IOCC combination of lead and titanium in various amounts to a glass reaction vessel containing phenol. Lead was supplied as lead (II) oxide ("PbO") and titanium as titanium(IV) oxide acetylacetonate ("TiO(acac)$_2$"). The components were heated to 100° C. for 3 hours in an approximately 6–7% oxygen in carbon monoxide atmosphere. The following results were observed:

| Experiment No. | Pd (dppb) $Cl_2$ mM | PbO Equivalents | TiO (acac)$_2$ Equivalents | Pd TON |
|---|---|---|---|---|
| 1 | .25 | 24 | 5.6 | 1847 |
| 2 | .25 | 50 | 5.6 | 2124 |

The various reaction conditions show that a Pd TON at least as high as 2124 can be obtained utilizing this catalyst system. Based on the results of these experiments, it is evident that a catalyst system containing Pd, a base, an onium chloride, Pb, and Ti can effectively catalyze the carbonylation reaction.

Example 2

The general procedure of Example 1 was repeated with 0.25 mM Pd(dppb)$Cl_2$, 600 equivalents of TBAC, 150 equivalents of NaOPh, and an IOCC combination of 50 equivalents of lead and 5.6 equivalents of manganese. Lead was supplied as PbO and manganese as manganese (III) acetylacetonate ("Mn(acac)$_3$"). The average Pd TON was found to be 2375, thus showing that the combination of Pd, base, onium chloride, Pb, and Mn can effectively catalyze the carbonylation reaction.

Example 3

The general procedure of Examples 1 and 2 was repeated with 0.25 mM Pd(dppb)Cl$_2$, 600 equivalents of TBAC, 150 equivalents of NaOPh, and an IOCC combination of 12 equivalents of copper and 5.6 equivalents of titanium. Copper was supplied as copper (II) acetylacetonate ("Cu(acac)$_2$") and titanium as TiO(acac)$_2$. The average Pd TON was found to be 4079, thus showing that the combination of Pd, base, onium chloride, Cu, and Ti can effectively catalyze the carbonylation reaction.

Example 4

The general procedure of Examples 1–3 was repeated with 0.25 mM Pd(dppb)Cl$_2$, 600 equivalents of TBAC, 150 equivalents of NaOPh, and an IOCC combination of 50 equivalents of copper and 12 equivalents of zirconium. Copper was supplied as Cu(cac)$_2$ and zirconium as zirconium (IV) butoxide ("Zr(OBu)$_4$"). The average Pd TON was found to be 2350, thus showing that the combination of Pd, base, onium chloride, Cu, and Zr can effectively catalyze the carbonylation reaction.

Comparative Example A

To show the comparative effectiveness of the previously detailed catalyst systems, replicate runs were conducted using the general procedure of Examples 1–4 with the following catalyst system components: 0.25 mM Pd(dppb)Cl$_2$, 600 equivalents of TBAC, and 50 equivalents of PbO. The results are shown below:

| Experiment No. | Pd (dppb) Cl$_2$ mM | PbO Equivalents | NaOPh Equivalents | Pd TON |
|---|---|---|---|---|
| 1 | .25 | 50 | 0 | 497 |
| 2 | .25 | 50 | 150 | 1623 |

These results illustrate that the catalyst systems of Examples 1 and 2 perform substantially better than the present system with or without added base at the conditions utilized.

Comparative Example B

Replicate runs were conducted using the general procedure of Examples 1–4 with the following catalyst system components: 0.25 mM Pd(dppb)Cl$_2$, 600 equivalents of TBAC, and 24 equivalents of Cu(acac)$_2$. The results are shown below:

| Experiment No. | Pd (dppb) Cl$_2$ mM | Cu (acac)$_2$ Equivalents | NaOPh Equivalents | Pd TON |
|---|---|---|---|---|
| 1 | .25 | 24 | 0 | 42 |
| 2 | .25 | 24 | 150 | 957 |

These results illustrate that the catalyst systems of Examples 3 and 4 perform substantially better than the present system with or without added base at the conditions utilized.

It will be understood that each of the elements described above, or two or more together, may also find utility in applications differing from the types described herein. While the invention has been illustrated and described as embodied in a method and catalyst system for producing aromatic carbonates, it is not intended to be limited to the details shown, since various modifications and substitutions can be made without departing in any way from the spirit of the present invention. For example, additional effective IOCC compounds can be added to the reaction. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A carbonylation catalyst system, comprising the following components:
   a Group VIII B metal source;
   a combination of inorganic co-catalysts including a lead source and at least one of a titanium source or a manganese source;
   an onium chloride composition; and
   a base.

2. The carbonylation catalyst system of claim 1, wherein the Group VIII B metal source is a palladium source.

3. The carbonylation catalyst system of claim 2, wherein the palladium source is a non-supported Pd(II) salt or complex.

4. The carbonylation catalyst system of claim 3, wherein the palladium source is dichloro(1,4-bis (diphenylphosphino)butane) palladium (II).

5. The carbonylation catalyst system of claim 1, wherein the onium chloride composition is tetrabutylammonium chloride.

6. The carbonylation catalyst system of claim 1, wherein the base is sodium phenoxide.

7. The carbonylation catalyst system of claim 1, wherein the combination of inorganic co-catalysts includes a lead source and a titanium source.

8. The carbonylation catalyst system of claim 1, wherein the combination of inorganic co-catalysts includes a lead source and a manganese source.

9. A carbonylation catalyst system, comprising the following components:
   a Group VIII B metal source;
   a combination of inorganic co-catalysts including a copper source and at least one of a titanium source or a zirconium source;
   an onium chloride composition; and
   a base.

10. The carbonylation catalyst system of claim 9, wherein the Group VIII metal source is a palladium source.

11. The carbonylation catalyst system of claim 10, wherein the palladium source is a non-supported Pd(II) salt or complex.

12. The carbonylation catalyst system of claim 11, wherein the palladium source is dichloro(1,4-bis (diphenylphosphino)butane) palladium (II).

13. The carbonylation catalyst system of claim 9, wherein the onium chloride composition is tetrabutylammonium chloride.

14. The carbonylation catalyst system of claim 9, wherein the base is sodium phenoxide.

15. The carbonylation catalyst system of claim 9, wherein the combination of inorganic co-catalysts includes a lead source and a titanium source.

16. The carbonylation catalyst system of claim 9, wherein the combination of inorganic co-catalysts includes a lead source and a zirconium source.

* * * * *